United States Patent [19]

Gustavsson et al.

[11] Patent Number: 4,563,176
[45] Date of Patent: Jan. 7, 1986

[54] DEVICE FOR STERILE STORAGE OF A CATHETER

[76] Inventors: Bengt Gustavsson, Bergsbogatan 29, Västra Frölunda, Sweden, 421 79; Johan Curelaru, Dr. Lindsgatan 3, Göteborg, Sweden, 413 25; Lars E. Linder, Varbergsvägen 319, Billdal, Sweden, 427 00

[21] Appl. No.: 532,027

[22] PCT Filed: Dec. 15, 1982

[86] PCT No.: PCT/SE82/00428
§ 371 Date: Aug. 10, 1983
§ 102(e) Date: Aug. 10, 1983

[87] PCT Pub. No.: WO83/02065
PCT Pub. Date: Jun. 23, 1983

[30] Foreign Application Priority Data

Dec. 18, 1981 [SE] Sweden ............................... 8107600

[51] Int. Cl.⁴ ............................................. A61M 5/32
[52] U.S. Cl. ..................................... 604/163; 604/171; 604/280
[58] Field of Search ..................... 604/51–53, 604/163, 165, 171, 283; 116/278; 33/126, 126.4, 126.5, 126.6

[56] References Cited

U.S. PATENT DOCUMENTS

| | | | |
|---|---|---|---|
| 4,168,699 | 9/1979 | Hauser | 604/171 |
| 4,235,232 | 11/1980 | Spaven et al. | 604/171 |
| 4,246,909 | 1/1981 | Wu et al. | 604/171 |
| 4,326,520 | 4/1982 | Alley | 604/171 |
| 4,392,853 | 7/1983 | Muto | 604/171 |

FOREIGN PATENT DOCUMENTS

| | | | |
|---|---|---|---|
| 2110009 | 5/1972 | France | 604/171 |
| 1257201 | 12/1971 | United Kingdom | 604/171 |

Primary Examiner—C. Fred Rosenbaum
Assistant Examiner—Michelle N. Lester
Attorney, Agent, or Firm—Holman & Stern

[57] ABSTRACT

A device for sterile storage of a catheter (11) and sterile advancing thereof a given length directly in a blood vessel, the device comprising a connecting piece (13), which is connectable both to a cannula and to a transparent, flexible protective sheath (15), in particular a plastic bag, enclosing the catheter. In order to allow continuous reading of the fed out catheter length the protective sheath (15) is equipped with a length scale (17), which has its highest value nearest the connecting piece (13) and which is made so that the reading of the length scale against the remaining length of the catheter in the protective sheath corresponds to the fed out length of the catheter. Further means (23;31;32;33) are provided which allow withdrawal of the protective sheath from wrinkled position to stretched position without bringing the catheter (11) with it.

12 Claims, 7 Drawing Figures

DEVICE FOR STERILE STORAGE OF A CATHETER

CROSS REFERENCE TO RELATED APPLICATION(S)

This U.S. application stems from PCT International Application No. PCT/SE82/00428 filed Dec. 15, 1982.

The present invention refers to a device for sterile storage of a catheter and sterile advancing thereof a given length directly in a blood vessel, and which apparatus comprises a connecting piece, which is both attachable to a cannula and to a transparent, flexible protective sheath, in particular a plastic bag.

BACKGROUND OF THE INVENTION

Use of catheters requires that several important prerequisites are fulfilled. The catheter must be kept sterile during insertion in a blood vessel. This means that during insertio the catheter cannot be exposed to the doctor's hands for example. Further it is very important that the free end of the catheter is positioned at the right place in the blood vessel and in order to do this one must know in advance how far in the catheter should be inserted. Until now the most common method has been using X-rays, but this method is complicated and can only be used if there is enough time available, which is not the case if the catheter is inserted during a major operation. For accidents and outside hospitals X-ray checking is entirely impossible and furthermore an incorrect or too deeply inserted catheter can result in serious complications such as puncture of the blood vessel or the catheter's entering the heart.

Investigations have been made to determine the average distance between different insertion points and the positions wheere the catheter point is desirably placed. These investigations have shown that for grown-ups the length variations are rather large, for example the distance between the insertion point in the right elbow vein and the right auricle of the heart is 48.8+ −6.0 cm (2 S.D) for women and 53.0+ −6.0 (2 S.D) for men. It is important that the point of the catheter arrives at the right position, and this is one of the reasons that a careful measurement of the insertion length of the catheter must be made.

It is known that one can make a printed scale on the catheter itself, but because the catheter has a diameter of about 1-2 mm it is very difficult to read. A printed scale on the outside of the catheter is furthermore quite inappropriate because any form of marking or ridging of the catheter itself increases the risk for causing thromboses as a result of accumulation of blood platelets at or in the roughnesses in the surface of the catheter. Further the printing ink can be partly or completely dissolved by the blood or rubbed off by friction against the blood vessel walls.

According to another proposal the catheter is wound up on a drum and by turning it in a circular holder the catheter can be fed out. The drum can be equipped with an index so that one can keep track of how many turns the drum has made and with knowledge of the circumference of the drum (in the present case 5 inches=127 mm) one can make a rough estimation of how much catheter has been fed out. However, one does not get a continuous length indication and one must continually calculate parts of turns into centimeters. The method is also only usable if the catheter is wound up on a drum.

Also known is a packaging of a catheter in the form of a plastic bag which is detachably affixed to a connecting piece, to which a cannula can also be affixed. The plastic bag allows handling of the catheter without its contamination, but this packaging does not allow measurement of how much the catheter has been advanced in the blood vessel.

SUMMARY AND ADVANTAGES OF THE INVENTION

The purpose of the present invention is to provide a simple device for sterile storage and advancing of a catheter which fulfills the following requirements:

1. it must be simple and inexpensive to manufacture since it is a throw-away product,
2. one must be able to easily read how far the catheter has been inserted into the blood vessel at any time during its insertion,
3. one must have a good finger feel during insertion of the catheter, so that if the catheter meets a resistance that is immediately felt by the fingers,
4. the catheter must be completely smooth and without markings which can cause complications,
5. the apparatus must be so constructed as not to leave any marks on the catheter,
6. the length indication must be clear, exact and easy to read,
7. it must be possible to draw the protective sheath back from wrinkled position to stretched position without bringing the catheter with it.

These problems have been solved by providing the protective sheath with a length scale which has its highest value nearest the connecting piece and which is made so that the reading of the length scale against the remaining length of the catheter in the protective sheath corresponds to the length of the fed out catheter and that means are arranged for providing withdrawal the protective sheath from wrinkled position to stretched position without simultaneously withdrawing the catheter, for example means for temporarily squeezing the catheter during the protective sheath's withdrawl and/or a means of providing a resilient stretching of the protective sheath.

DESCRIPTION OF EMBODIMENTS

Figure 1:
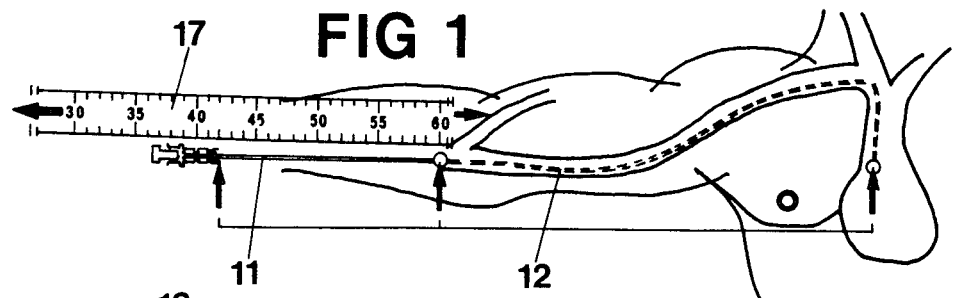
FIG. 1 shows schematically the blood path in the upper arm and breast with the catheter in veins which are often used for catheterization.

In FIG. 1 the idea of the invention is shown schematically, namely how one can easily keep track of how much of the catheter 11 has been inserted in the blood vessel 12 under sterile conditions.

Figure 2:
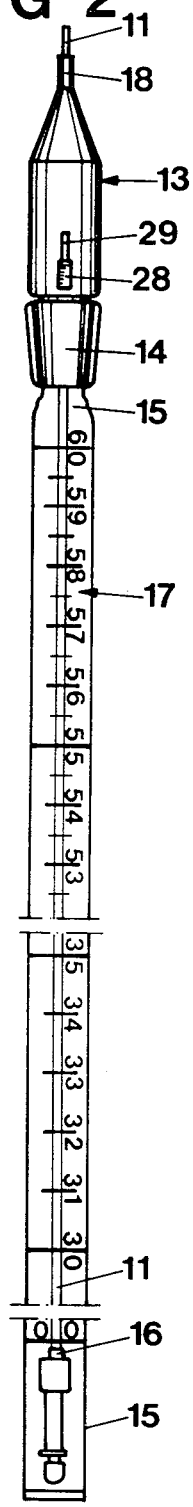
FIG. 2 shows a view from above of the apparatus according to the invention in full scale.

In FIG. 2 is shown in approximately full scale an embodiment of the device according to the invention, where 11 is the catheter, 13 a connecting piece, 14 a terminal cone which can be squeezed onto the connecting piece and to which is attached a container 15 in the form of a protective sheath. It has a somewhat greater length than the catheter 11. To it is fastened a coupling piece 16 to the free end of which a cannula or an infusion apparatus or the like can be attached. The protective sheath 15 can appropriately be made of a flexible, transparent material, for example a plastic bag, through which the position of the catheter can be observed. A scale 17 is placed on the protective sheath, the zero of which is given and which is placed furthest down in the bag at the level of the coupling piece's 16 coupling to the catheter 11, while nearest the terminal cone 14 the length scale has its highest value, for example 60 cm.

During insertion of the catheter, after the usual puncture of the vein using a cannula (not shown) which is attached to the connecting piece's 13 front end 18, the catheter is gripped via the protective sheath 15 with two fingers and both are pushed in the direction of the terminal cone 14, whereby the protective sheath is wrinkled and the catheter is fed out a distance. An insertion length of several cm at a time is appropriate and after each push forward of the catheter the protective sheath is drawn back again so that the coupling piece's 16 position on the scale 17 can be read. In FIG. 1 for example the catheter has been inserted far enough that the coupling piece is opposite the marking 42 cm, on the scale 17, which means that the catheter has been inserted that distance.

Figure 3:
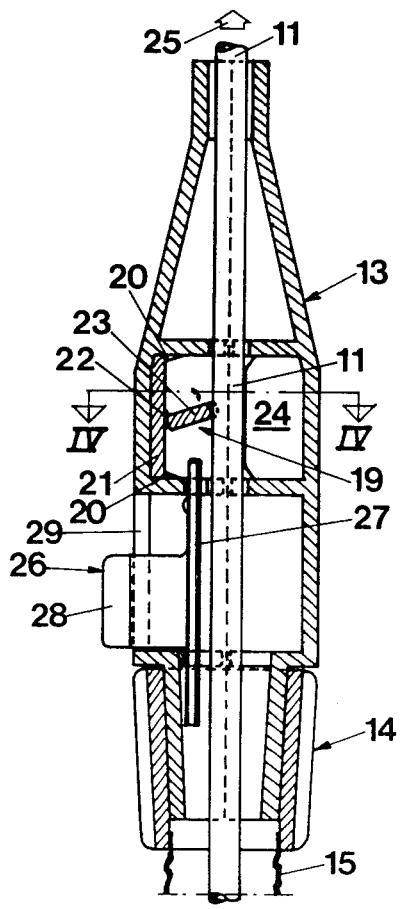
FIG. 3 shows a cross section through a connecting piece.
Figure 4:
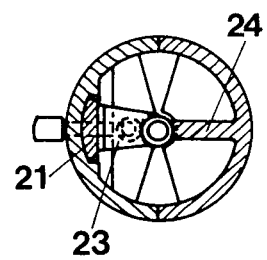
FIG. 4 is a cross section through the line IV—IV in FIG. 3.

Because it is desirable that the connecting piece gives as little friction as possible on the catheter, withdrawal of the protective sheath will also withdraw the catheter to a large extent, which is very difficult to avoid because the catheter is not reachable by other means than via the protective sheath. For this purpose the connecting piece 13 is appropriately equipped with means 19 of some kind, which at least temporarily prevents withdrawal of the catheter when the protective sheath is withdrawn. Such means 19 can be made in a number of ways and an apparatus is shown in FIG. 3 and 4. The apparatus consists of a holding plate 21 snapped in place behind lips 20 in the connecting piece 13 in which a ratchet 23 somewhat longer than the distance to the catheter 11 is fastened via a hinge 22. Opposite the ratchet 23 on the opposite side of the catheter is a fixed support plate 24 which prevents the catheter from moving sideways.

During movement of the catheter 11 in the direction of the arrow the ratchet also will rotate in the same direction and the catheter can be pushed through the connecting piece 13 without significant friction. Should the catheter be drawn in the opposite direction the ratchet 23 will swing on its hinge in the same direction and press the catheter against the support plate 24, whereby the continued motion of the catheter is blocked. On further motion forward in the direction of the arrow 25 the ratchet will swing away from the catheter and free it.

In some cases it can be desirable to discontinue the function of the ratchet 23, for example if the catheter is to be withdrawn a little in order to get past a hindrance or the like and for that purpose the connecting piece 13 is equipped with a releasing mechanism 26 in the form of a rod 27 and a handle 28 which passes through a slit 29 in the connecting piece 13. The rod 27 is movable axially using the handle 28 toward the ratchet 23 which can be swung away from its grip on the catheter 11.

Figure 5:
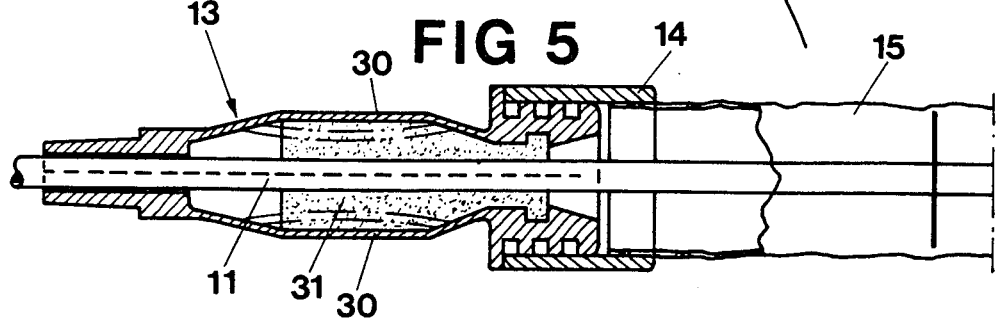
FIG. 5 shows a cross section through a connecting piece according to a modified embodiment.

In FIG. 5 is shown a different embodiment of means for preventing the withdrawal of the catheter together with the protective sheath and which is used with a connecting piece 13 in the same way as in the embodiment according to FIG. 3 and 4. For the embodiment according to FIG. 3 and 4 the whole connecting piece is made of a hard plastic which cannot be deformed manually. Such is also the case with the connecting piece according to FIG. 5 with the difference that at least one, and in the shown embodiment two opposite parts 30 are formed with a thinner wall maerial so that they can be pressed together towards the catheter 11. The pressure from the parts 30 is appropriately transmitted via a compression layer 31, for example of a foam plastic material, to the catheter. The compression layer 31 also has the function of preventing blood from passing further backwards in the direction of the protective sheath 15.

Both the connecting piece 13 and the compression layer are divided so that these pieces can be removed after the catheter has been placed in the right position.

Figure 6:
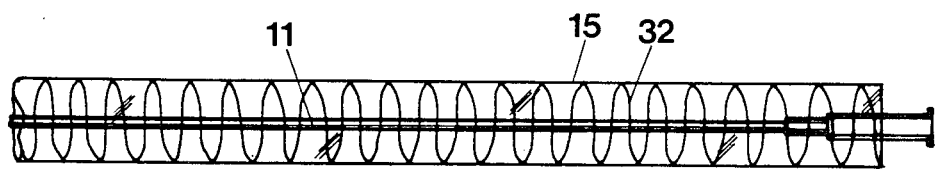
FIG. 6 shows schematically a part of the protective sheath according to a modified embodiment.

In some cases it can be advantageous to provide the protective sheath 15 with means which tries to hold it or at least its front part nearest the insertion instrument in a stretched position. Such a means can be for example a soft but resilient spiral reinforcement 32 of the walls of the protective sheath as shown in FIG. 6.

Figure 7:
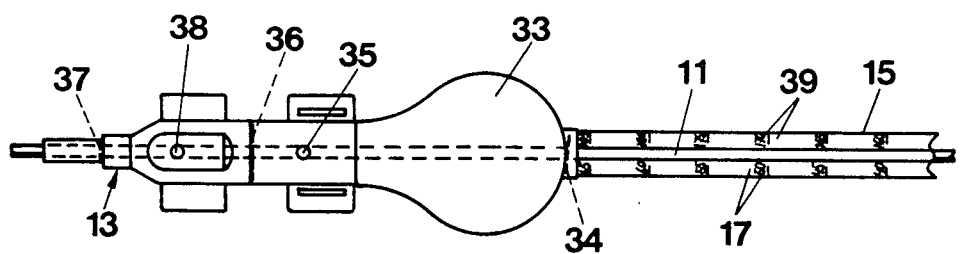
FIG. 7 shows a view from above of a further embodiment of the device according to the invention.

Another possibility is to hold the protective sheath 15 in the stretched position by pumping air into it when required. Such a means is shown in FIG. 7 where between the protective sheath 15 and the connecting piece 13 is arranged a compressible bag 33 of elastic material. A nonreturn valve 34 is arranged between the bag 33 and the protective sheath 15 and allows passage of air into the protective sheath but closes in the opposite direction. Another nonreturn valve 35 is arranged on the connecting piece 13 in front of the bag or alternatively on the bag itself for sucking air into it.

On pumping the bag 33 air is pressed into the protective sheath 15 which holds it in the resiliently stretched position. A light pumping is appropriate after each feeding out of the catheter 11 so that the protective sheath automatically returns to the stretched position without bringing the catheter back with it.

In order to prevent air from being pressed forward into the connecting piece 13 and the cannula the connecting piece is equipped with seals 36, 37 against the catheter 11 and with an air escape hole 38 between the seals.

In extensive tests it was found that there is a very good correlation between the height of the patient and the distance between the insertion point of the catheter, for example at the elbow vein, and the point where the tip of the catheter is desirably placed, for example the right auricle of the heart. It can therefore be appropriate that the protective sheath 15 is provided with a graduation 39 (FIG. 7) which is based on the height of the patient and directly correlates with the catheter length which is to be fed out, in addition to the scale 17 which shows the length of catheter which has been fed out.

We claim:

1. A device for sterile storage of a catheter and sterile advancing of a given length thereof directly into a blood vessel, comprising a cannula, a catheter, a transparent, flexible sheath enclosing said catheter, and a connecting piece, through which said catheter is fed, coupling said cannula to said protective sheath, wherein the protective sheath is provided with a length scale which has its highest value nearest the connecting piece and which is so arranged that the reading of the length scale against the catheter length remaining in the protective sheath corresponds to the fed out catheter length; and means for allowing extension of the protective sheath from a wrinkled to a stretched position without simultaneous withdrawal of the catheter.

2. The device according to claim 1, wherein said means for allowing extension comprise at least one ratchet member rotatably coupled to said connecting piece, the length of said ratchet member being greater than the distance between said connecting piece and said catheter so that one end of said ratchet member rests against said catheter, whereby feeding out of said catheter is allowed but on motion of the catheter in the opposite direction said ratchet member rotates to an active position so as to engage the catheter and impede its further motion backwards.

3. The device according to claim 1, wherein said connecting piece includes at least two elements which, when manually compressed, temporarily block the forward feeding of the catheter.

4. The device according to claim 1, wherein at least one side wall of the connecting piece is resiliently deformable under applied pressure.

5. The device according to claim 2, wherein the connecting piece includes a slidable rod member engageable with said ratchet member to displace the same from engagement with said catheter.

6. The device according to claim 1, wherein said means for allowing extension comprises a spiral shaped member resiliently reinforcing the walls of the protective sheath.

7. The device according to claim 1, wherein the connecting member includes a compressible, elastomeric bag coupled to the protective sheath and at least two one-way valves arranged so as to allow passage of air from the bag into the protective sheath and suction of air into the bag respectively, whereby through pumping the bag, air is pressed into the protective sheath holding it in its resiliently stretched position.

8. The device according to claim 7, wherein the connecting piece further includes at least one seal adapted to engage the catheter.

9. The device according to claim 8, wherein the protective sheath is further provided with a graduated scale based on the height of the patient and which directly correlates with the appropriate length of fed out catheter.

10. The device of claim 8, wherein the connecting piece further includes an air escape hole.

11. The device of claim 1 wherein said means for allowing extension of the protective sheath comprises means for temporarily squeezing the catheter during withdrawal of the protective sheath.

12. The device of claim 1 wherein said means for allowing extension of the protective sheath comprises a means for providing resilient stretching of the protective sheath.

* * * * *